US008465754B2

(12) United States Patent
Watanabe et al.

(10) Patent No.: US 8,465,754 B2
(45) Date of Patent: Jun. 18, 2013

(54) *BORDETELLA PARAPERTUSSIS* WHOLE-CELL VACCINE COMPOSITION

(75) Inventors: Mineo Watanabe, Saitama (JP); Eiji Komatsu, Saitama (JP)

(73) Assignee: Kitasato Daiichi Sankyo Vaccine Co., Ltd., Saitama (JP)

( * ) Notice: Subject to any disclaimer, the term of this patent is extended or adjusted under 35 U.S.C. 154(b) by 0 days.

(21) Appl. No.: 12/601,795

(22) PCT Filed: May 28, 2008

(86) PCT No.: PCT/JP2008/059777
§ 371 (c)(1),
(2), (4) Date: May 19, 2010

(87) PCT Pub. No.: WO2008/146830
PCT Pub. Date: Dec. 4, 2008

(65) Prior Publication Data

US 2010/0260803 A1 Oct. 14, 2010

(30) Foreign Application Priority Data

May 28, 2007 (JP) ................................ 2007-140721

(51) Int. Cl.
*A61K 39/10* (2006.01)

(52) U.S. Cl.
USPC ...................... 424/254.1; 424/253.1; 435/243

(58) Field of Classification Search
None
See application file for complete search history.

(56) References Cited

U.S. PATENT DOCUMENTS

| | | | |
|---|---|---|---|
| 2,655,583 | A | 10/1953 | Souter |
| 6,964,767 | B2 | 11/2005 | Guiso-Maclouf et al. |
| 7,070,779 | B2 | 7/2006 | Boursaux-Eude et al. |
| 7,314,910 | B2 | 1/2008 | Boursaux-Eude et al. |

FOREIGN PATENT DOCUMENTS

| | | |
|---|---|---|
| EP | 1043029 | 10/2000 |
| JP | 10507347 | 7/1998 |
| JP | 11510793 | 9/1999 |
| JP | 2000351735 | 12/2000 |
| JP | 2002544169 | 12/2002 |
| JP | 2003533990 | 11/2003 |
| WO | 9611258 | 4/1996 |
| WO | 9702835 | 1/1997 |
| WO | 0067785 | 11/2000 |
| WO | 2007111326 | 10/2007 |

OTHER PUBLICATIONS

Watanabe et al (Vaccine, v 19, n 9-10, p. 1199-1203, Dec. 8, 2001).*
Long et al (Proc.Royal Soc. Of Bio. Sciences.. "Acellular pertussis vaccination facilitates *Bordetella parapertussis* infection in a rodent model of bordetellosis". 2010. pp. 1-9).*
Griffiths, "Efficacy of Whole-Cell Pertussis Vaccine", In Pathogenesis and Immunity in Pertussis, 1988, pp. 354-355.
Khelef et al., "*Bordetella pertussis* and *Bordetella parapertussis*: Two Immunologically Distinct Species", Infection and Immunity, Feb. 1993, vol. 61, No. 2, pp. 486-490.
Kohler-Kubelka et al., "Diphtheria-tetanus-pertussis vaccine combined with *Bordetella parapertussis* vaccine", Journal of Hygiene, 1962, vol. 60, pp. 289-293.
Liese et al., "Clinical and epidemiological picture of *B pertussis* and *B parapertussis* infections after introduction of acellular pertussis vaccines", Archives of Disease in Childhood, 2003, vol. 88, pp. 684-687.
Mastrantonio et al., "*Bordetella parapertussis* Infections", Pertussis Vaccine Trials, Developments in Biological Standardization, 1997, vol. 89, pp. 255-259.
Saran et al., "Serological and protective activities of pertussis, parapertussis and bronchiseptica vaccines", Indian Journal of Medical Research, Dec. 1981, vol. 74, pp. 815-820.
Watanabe et al., "Reciprocal Protective Immunity against *Bordetella pertussis* and *Bordetella parapertussis* in a Murine Model of Respiratory Infection", Infection and Immunity, Nov. 2001, vol. 69, No. 11, pp. 6981-6986.
Watanabe et al., "Whooping cough due to *Bordetella parapertussis*: an unresolved problem", Expert Review of Anti-Infective Therapy, 2004, vol. 2, No. 3, pp. 447-454.
International Search Report for PCT/JP2008/059777 dated Jun. 23, 2008.
Ungar, Jr., "Recent Advances in Pertussis Immunisation", The Irish Journal of Medical Science, Apr. 1952, 6 (316)145-159.
Supplemental European Search Report for EP08764793 dated Nov. 16, 2012.

* cited by examiner

*Primary Examiner* — Jennifer Graser
(74) *Attorney, Agent, or Firm* — Andrus, Sceales, Starke & Sawall, LLP

(57) ABSTRACT

An objective of the present invention is to provide a whole-cell bacterial vaccine composition for preventing whooping cough caused by *Bordetella parapertussis*, comprising whole cells, whole-cell homogenate, or cell lysate of *B. parapertussis* as an immunogen, and methods for producing them.

2 Claims, 6 Drawing Sheets

| Vaccine | Effectiveness against *B. parapertussis* |
|---|---|
| Existing DTaP vaccine | Ineffective |
| Whole-cell pertussis vaccine wP | Ineffective |
| *B. parapertussis* vaccine | Effective |

| Dose of the vaccine (Mice) | Corresponding dose in humans (predicted from correlation) | Effectiveness |
|---|---|---|
| 0.125 mL (Dose 1) | 0.5 mL | Effective |
| 0.042 mL (Dose 0.3) | 0.167 mL | Effective |
| 0.0125 mL (Dose 0.1) | 0.05 mL | Effective |
| 0.0042 mL (Dose 0.03) | 0.0167 mL | Effective |

*BORDETELLA PARAPERTUSSIS* WHOLE-CELL VACCINE COMPOSITION

CROSS-REFERENCE TO RELATED APPLICATIONS

This application is the U.S. national stage of International Application No. PCT/JP2008/059777, filed on May 28, 2008, and published on Dec. 4, 2008, as International Publication No. WO 2008/146830 in the Japanese language, which application claims priority to Japanese Patent Application No. 2007-140721, filed on May 28, 2007.

TECHNICAL FIELD

The present invention relates to a whole-cell bacterial vaccine composition for preventing whooping cough caused by *Bordetella parapertussis*, comprising whole cells, whole-cell homogenate, or cell lysate of *B. parapertussis* as immunogen, and methods for producing them. Furthermore, the present invention relates to methods for preventing whooping cough caused by *B. parapertussis*, comprising the step of administering whole cells, whole-cell homogenate, or cell lysate of *B. parapertussis*, to a subject.

BACKGROUND ART

Whooping cough (pertussis) is a respiratory infection of which the predominant symptom is coughing, and is caused by the infection of *Bordetella pertussis* or *Bordetella parapertussis*. Patients suffer from coughing spasms over a prolonged period (two weeks to several months). Since a large proportion of whooping cough cases are caused by *B. pertussis*, vaccines have been developed targeting *B. pertussis*, and with the current wide circulation of effective and safe vaccines, the number of whooping cough patients and the number of deaths have both greatly decreased.

*B. parapertussis* and *B. pertussis* belong to the genus *Bordetella*, and are both aerobic bacteria whose host is human. The virulence factors (adenylate cyclase toxin, necrosis toxin, tracheal cytotoxin, filamentous hemagglutinin, and such) produced by both bacteria are highly homologous and their mechanisms of pathogenesis are considered to be almost the same. They have similar auxotrophy and their optimum culture conditions are also almost the same. A difference between the two bacteria is seen in the production of pertussis toxin (produced only by *B. pertussis*), and this may be related to the predominant prevalence of *B. pertussis*.

According to recent research, whooping cough caused by *B. parapertussis* infection is not very different in seriousness from that caused by *B. pertussis*, and is also widely spread throughout the world. On the other hand, despite the very high homology between *B. parapertussis* and *B. pertussis*, current pertussis vaccines (produced from *B. pertussis*) have been found to have little or no effect on *B. parapertussis* (Non-Patent Documents 1 to 3). Furthermore, there are reports that while natural immunity acquired through cure of the infection causes cross-reactions, the existing vaccines do not provide cross-protection against both bacteria (Non-Patent Documents 3 to 5). These results strongly indicate that if the increasing control of *B. pertussis* using the existing vaccines results in the decrease of *B. pertussis* distributed in nature, this may increase the prevalence of *B. parapertussis*.

At present, studies have been done on whooping cough vaccines produced using a mutant *Bordetella* strain as immunogen (Patent Document 1), vaccines related to pertactin, which is an outer membrane protein expressed by *B. parapertussis* (Patent Document 2), and such. However, their actual effects on whooping cough caused by *B. parapertussis* are unclear, and there are no known vaccines that may provide effective protection against whooping cough caused by *B. parapertussis* infection. Furthermore, it is difficult to run an evaluation system for vaccines effective for *B. parapertussis*, which has not been successful so far.

Moreover, as is evident from the fact that development of novel whole-cell vaccines has ended up in failure for many pathogens such as *Shigella, Neisseria gonorrhoeae, Neisseria meningitidis*, and malaria, it is very difficult to develop and produce an effective whole-cell *B. parapertussis* vaccine (Non-Patent Document 6).

Accordingly, there is a demand for the development of vaccines that may effectively regulate the activity of *B. parapertussis*.

Prior art documents related to the present invention are shown below.

[Patent Document 1] Japanese Patent No. 2655583

[Patent Document 2] Japanese Patent Application Kohyo Publication No. (JP-A) 2003-533990 (unexamined Japanese national phase publication corresponding to a non-Japanese international publication

[Non-Patent Document 1] Liese, J. G. et al. Arch Dis Chid 88(8): 684-687, 2003

[Non-Patent Document 2] Mastrantonio, P. et al. Dev Biol Stand 89: 255-259, 1997

[Non-Patent Document 3] Watanabe, M. and Nagai, M. Expert Rev Anti-infect Ther 2(3): 447-454, 2004

[Non-Patent Document 4] Khelef, N. et al. Infect Immun 61(2): 486-490, 1993

[Non-Patent Document 5] Watanabe, M. and Nagai, M. Infect Immun 69(11): 6981-6986, 2001

[Non-Patent Document 6] Griffiths, E. In Pathogenesis and Immunity in Pertussis. P. 354-355. 1988

DISCLOSURE OF THE INVENTION

Problems to be Solved by the Invention

The present invention was achieved in view of the above circumstances. An objective of the present invention is to provide a whole-cell bacterial vaccine composition for preventing whooping cough caused by *Bordetella parapertussis*, comprising whole cells, whole-cell homogenate, or cell lysate of *B. parapertussis* as an immunogen, and methods for producing them.

Another objective of the present invention is to provide methods for preventing whooping cough caused by *B. parapertussis*, comprising the step of administering whole cells, whole-cell homogenate, or cell lysate of *B. parapertussis*, to a subject.

Live *B. parapertussis* cells are highly virulent and cannot be inoculated directly, and the large variety of toxins produced by the bacteria must first be inactivated. However, determining the conditions for inactivation is very difficult. Strong conditions such as using a high concentration of a common inactivator completely destroy the virulence of the bacteria, but also cause loss of the vaccine effect at the same time. On the other hand, weak conditions such as using low inactivator concentrations tend to increase the vaccine effect, but the remaining bacterial virulence may render the vaccine harmful, leading to the death of vaccinated animals etc. Although the inactivation of whole-cell vaccines, particularly whole-cell pertussis vaccines produced from *B. pertussis*, which is related to *B. parapertussis*, is carried out using approximately 0.5% formaldehyde, it was not possible to prepare an effective *B. parapertussis* vaccine using this condition.

Means for Solving the Problems

To solve the above-mentioned problems, the present inventors carried out dedicated research. *B. pertussis* carries a powerful toxin called pertussis toxin, which is involved in the side-effects and toxicity of *B. pertussis* vaccines. However, *B. parapertussis* does not have the pertussis toxin, and therefore, the present inventors considered the virulence of *B. parapertussis* to be low. Furthermore, the present inventors discovered using a murine experimental system that *B. parapertussis* is eliminated from the living body more rapidly than *B. pertussis* (FIG. 6). Therefore, they postulated that even if vaccines were produced with a low concentration of formalin, it should be possible to make effective vaccines showing no toxicity using *B. parapertussis*.

Specifically, *B. parapertussis* was first cultured at 37° C. for three days, then adjusted to a cell concentration of $10^{10}$ cells/mL, and inactivated by adding a formaldehyde solution at a final formaldehyde concentration of 0.2%. The cells were adjusted to be equivalent to a cell concentration of $10^{10}$ cells/mL by adding sterilized physiological phosphate buffered saline, to obtain a vaccine composition.

Mice (3.5 weeks old) were subcutaneously inoculated with 0.125 mL (equivalent to ¼ single human dose (SHD)) of the vaccine composition, and 14 days later, a booster inoculation (the same amount) was carried out. Fourteen days following the booster inoculation, the mice were transnasally infected with a *B. parapertussis* suspension (a viable cell concentration of approximately $10^8$ CFU/mL, 50 μL/mouse) under pentobarbital anesthesia. As a result, the mice inoculated with the vaccine composition of the present invention showed a decrease in the number of viable bacterial cells in the lungs as compared to the mice of the negative control group that was not vaccinated, demonstrating the high infection-protective activity of the vaccine. Furthermore, examination of the inoculum dose of the vaccine composition revealed that the composition showed a protective activity against *B. parapertussis* infection even at 1/30 of the usual dose of pertussis vaccines.

Thus, the present inventors succeeded in producing a whole-cell bacterial vaccine composition for preventing whooping cough caused by *B. parapertussis*, which has a protective activity against *B. parapertussis* infection and comprises whole cells, whole-cell homogenate, or cell lysate of *B. parapertussis* as an immunogen, and thereby completed the present invention.

More specifically, the present invention provides:

[1] a whole-cell bacterial vaccine composition for preventing whooping cough caused by *Bordetella parapertussis*, comprising whole cells, whole-cell homogenate, or cell lysate of *B. parapertussis*, as immunogen;

[2] the vaccine composition of [1], wherein the antigen is obtained by the steps of:

(a) culturing *B. parapertussis* cells at 37° C. for one to three days to produce a *B. parapertussis* culture preparation with a final cell concentration of $10^{10}$ cells/mL; and (b) inactivating the whole *B. parapertussis* cell by adding an inactivator to the *B. parapertussis* culture preparation;

[3] the vaccine composition of [1], wherein the antigen is obtained by the steps of:

(a) culturing a *B. parapertussis* cell at 37° C. using the amount of filamentous hemagglutinin (FHA) as an index to produce a *B. parapertussis* culture preparation with a final cell concentration of $10^{10}$ cells/mL; and (b) inactivating the whole *B. parapertussis* cell by adding an inactivator to the *B. parapertussis* culture preparation;

[4] the vaccine composition of [2] or [3], wherein the inactivation of *B. parapertussis* cells is carried out by a formalin solution comprising formaldehyde at a final concentration of 0.1 to 0.2%;

[5] the vaccine composition of any one of [1] to [4], wherein the *B. parapertussis* is an antibiotic-resistant mutant;

[6] the vaccine composition of any one of [1] to [5], wherein an effective dose in mice is 0.100 mL/kg body weight to 3 mL/kg body weight when the final cell concentration of vaccine formulation is adjusted to $10^{10}$ cells/mL;

[7] the vaccine composition of any one of [1] to [5], wherein an effective single dose in humans is 0.02 mL to 0.5 mL when the final cell concentration of vaccine formulation is adjusted to $10^{10}$ cells/mL;

[8] the vaccine composition of any one of [1] to [7], wherein the composition is administered once or multiple times;

[9] a method for producing a vaccine composition, comprising the steps of:

(a) culturing *B. parapertussis* cells at 37° C. for one to three days to produce a *B. parapertussis* culture preparation with a final cell concentration of $10^{10}$ cells/mL;

(b) inactivating the whole *B. parapertussis* cells by adding an inactivator to the *B. parapertussis* culture preparation; and (c) mixing the inactivated whole *B. parapertussis* cells with a pharmaceutically acceptable additive;

[10] a method for producing a vaccine composition, comprising the steps of:

(a) culturing *B. parapertussis* cells at 37° C. using the amount of filamentous hemagglutinin (FHA) as an index to produce a *B. parapertussis* culture preparation with a final cell concentration of $10^{10}$ cells/mL;

(b) inactivating the whole *B. parapertussis* cells by adding an inactivator to the *B. parapertussis* culture preparation; and (c) mixing the inactivated whole *B. parapertussis* cells with a pharmaceutically acceptable additive;

[11] a method for preventing whooping cough caused by *B. parapertussis*, comprising the step of administering whole cells, whole-cell homogenate, or cell lysate of *B. parapertussis*, to a subject; and

[12] a method for inducing immunity against *B. parapertussis* in a subject, comprising the step of administering whole cells, whole-cell homogenate, or cell lysate of *B. parapertussis*, to a subject.

MODE FOR CARRYING OUT THE INVENTION

The present invention relates to a whole-cell bacterial vaccine composition for preventing whooping cough caused by *Bordetella parapertussis*, comprising a whole cell, whole-cell homogenate, or cell lysate of *Bordetella parapertussis* as an immunogen.

The *B. parapertussis* vaccine formulation of the present invention is produced by culturing and collecting bacterial antigens, and then inactivating the antigens according to the production method described later.

In the present invention, bacterial strains purified from clinically isolated strains of *B. parapertussis* or such can be used for culture, or alternatively, artificial mutants of these bacterial strains can be used. *Bordetella parapertussis* is preferably used as bacterial seed, and the 23054 strain, which is a clinical isolate of this species, is more preferred.

Furthermore, the bacterial strain to be used in the present invention may be an antibiotic-resistant mutant. When an antibiotic-resistant mutant is used, an antibiotic can be added to the culture medium to prevent contamination by other bacteria. The antibiotic is not particularly limited so long as it is well known to those skilled in the art, but is preferably nalidixic acid or streptomycin, or more preferably streptomycin.

Specific examples of the bacterial strains that can be used in the present invention include a mutant strain of the clinical isolate 23054 strain that has adapted to a streptomycin-containing medium. This mutagenesis and selection were carried out by the present inventors at the Kitasato Institute. Since this mutant is a clinical isolate and maintains its virulence, and its streptomycin-resistance mutation allows the avoidance of bacterial contamination even in long-term cultures spanning several days, it is preferably used in the present invention.

The streptomycin-resistant mutant of *Bordetella parapertussis* strain 23054, BPP23054SMR, has been deposited by the Applicants as shown below:

(a) Name and address of the depository institution

Name: National Institute of Technology and Evaluation (NITE), Patent Microorganisms Depositary (NPMD)

Address: 2-5-8 Kazusa Kamatari, Kisarazu, Chiba, Japan (postal code 292-0818)

(b) Date of submission: May 8, 2007

(c) Depository number: NITE BP-356

Antigens in the vaccine compositions of the present invention can be obtained by steps (a) and (b) below:

(a) culturing *B. parapertussis* at 37° C. for one to three days to produce a *B. parapertussis* culture preparation with a final cell concentration of $10^{10}$ cells/mL; and (b) inactivating the whole *B. parapertussis* cells by adding an inactivator to the *B. parapertussis* culture preparation.

Antigens in the vaccine compositions of the present invention can also be obtained by steps (a) and (b) below:

(a) culturing *B. parapertussis* at 37° C. using the amount of filamentous hemagglutinin (FHA) as an index to produce a *B. parapertussis* culture preparation with a final cell concentration of $10^{10}$ cells/mL; and (b) inactivating the whole *B. parapertussis* cells by adding an inactivator to the *B. parapertussis* culture preparation.

The step of culturing *B. parapertussis* to produce a *B. parapertussis* culture preparation in the method for producing a vaccine formulation of the present invention is described below.

When *B. parapertussis* is cultured as a bacterial seed in the present invention, the bacterial cells are spread on a Bordet-Gengou medium and incubated at 37° C. for three days. From the produced colonies, those showing a hemolytic zone are further spread on a charcoal agar medium and incubated at 37° C. for one day. Thereafter, cells are further passaged on a charcoal agar medium and cultured at 37° C. for three days (one to three days) for enrichment. Since continuous culture of *B. parapertussis* causes a decrease in growth due to bacteriolysis, it is desirable to collect the cells before they lyse.

Furthermore, the *B. parapertussis* cells used as antigen are preferably virulent. Virulent *B. parapertussis* cells can be collected by using as an index, for example, the amount of filamentous hemagglutinin (FHA), which is a virulence factor. The presence or absence of FHA can be confirmed by examining the hemagglutination reaction in a culture solution using methods well known to those skilled in the art.

Not only the above-described medium, but also a medium with any composition can be used for the vaccine production of the present invention so long as the composition is suitable for bacterial cell growth. The medium may contain a carbon source, nitrogen source, phosphate source, trace metals, and such. A preferred medium composition includes the medium described in the Examples. Furthermore, the above-mentioned medium may be a commercially available product. Preferred examples of commercially available media that can be used to culture *B. parapertussis* include Bordet-Gengou agar base and Charcoal agar (both from Beckton, Dickinson, and Company, U.S.A.), but are not limited thereto.

Furthermore, the medium may be supplemented with additives that adsorb and remove growth inhibitors for *B. pertussis* and *B. parapertussis*, such as ion exchange resins and cyclodextrin.

Culture containers that can be used in the bacterial culture in the present invention include glass containers, stainless steel containers, plastic containers, and commercially available fermentors.

The incubation temperature for the cell culture of the present invention is normally 35-37° C., but is particularly preferably 37° C.

The pH range for culturing *B. parapertussis* in the present invention is normally 7 to 7.5, but is not particularly limited to this pH. The culturing can also be carried out under acidic or basic conditions under which the bacterial cells do not die.

When *B. parapertussis* cells are enriched, the number of *B. parapertussis* cells is measured as necessary to confirm culture progress. The number of cells may be determined after short-term incubation by measuring the absorbance or turbidity at the wavelength of 650 nm. Nowadays it can also be determined from the number of DNA copies using quantitative PCR. Culture, collection, washing, and purification of *B. parapertussis* must be performed in an environment that allows strict containment. Normally, a Biosafety Level 2 (BSL2) environment as determined by the National Institute of Infectious Diseases is required.

In the step of producing a *B. parapertussis* culture preparation, the above method of culture is followed by washing, purification, and concentration of whole-cell antigens. The methods for washing, purification, and concentration are described below.

After culturing, the bacterial cells are washed and purified using phosphate buffered saline and such. Purification may be carried out using methods including, but not limited to, washing, centrifugation, stirring, concentration, and column methods.

The timing of washing, purification, and concentration is preferably before inactivation, but may even be carried out after inactivation, or both before and after inactivation.

In the methods of the present invention for producing vaccines, the step of inactivating a *B. parapertussis* culture preparation or such by adding an inactivating regent to the *B. parapertussis* culture preparation or such will be described below.

Various methods can be used to inactivate antigens, but generally, the optimal inactivation method differs depending on whether the antigen is a whole bacterial cell or a protein. Inactivation can be carried out by various chemical treatments and physicochemical treatments. As an example, inactivation includes the following, but is not limited thereto.

Examples of chemical treatment substances that may be used to treat bacteria for the purpose of inactivation include the following substances. Applicable concentrations are shown, but they are not limited thereto:

formaldehyde (0.04-4%), phenol (0.1-5 v/v %), chloroform (10-60 v/v %), acetone (10-80 v/v %), and SH reagent (1-100 mM);

hydrogen peroxide (0.1-5%), peracetic acid (0.5-10 w/v %), and carbon dioxide (5-90 v/v %); and ozone (0.1-10 v/v %) and surfactant (0.01-5 w/v %).

Physicochemical treatment method for inactivation can be carried out by taking the following measures. Examples of applicable conditions are shown below, but they are not limited thereto:

Heating (temperature: 30-70° C.; heating time: 10-120 minutes), γ-ray irradiation (radiation source: cobalt 60; 5-50 kGy (kiloGray)), laser light irradiation (light source: various laser irradiation equipment; wavelength: 500-700 nm; intensity of light: 0.01-1 J (Joule)/$cm^2$), electron beam irradiation (microwave oven), ultrasound irradiation and the like.

The treatment conditions are not fixed, and the amount of bacteria cells, temperature, buffer pH, treatment period, and such can be varied to set up suitable conditions. Treatment is generally carried out under sterile conditions.

These inactivation methods can be used singly or in combination. Since the presence of amino acids or amines during inactivation may result in improvement and stabilization of the quality of inactivated preparations, these substances may be supplemented as necessary. Also, in addition to inactivation by formalin, additional application of organic solvent treatment, heating, and γ-ray irradiation treatment can yield inactivated whole bacteria that have a stable quality because of their low bacteriolysis activity.

Since *B. pertussis* inactivated using a low concentration of formaldehyde retains virulence, inactivation is conventionally done using a high concentration of formaldehyde. While *B. pertussis* inactivated using a high formaldehyde concentration still shows effectiveness as a vaccine, *B. parapertussis* inactivated using a high formaldehyde concentration loses its effectiveness. Therefore, inactivation treatment of *B. parapertussis* using formaldehyde is considered to be difficult.

The present inventors focused on the fact that *B. parapertussis* does not possess the pertussis toxin and has a relatively low virulence compared to *B. pertussis* (FIG. 6), and treated it with a low concentration of formaldehyde under appropriate conditions. As a result, they succeeded for the first time in producing a vaccine composition having low virulence while showing a vaccine effect. Table 1 shows the effectiveness and virulence of the vaccines produced by using different formaldehyde concentrations.

TABLE 1

| Vaccine | Formaldehyde concentration (%) at the time of inactivation | Efficacy | Mouse fatality rate |
|---|---|---|---|
| *Bordetella* | 0 | unknown | 100% (5/5) |
| *pertussis* | 0.2 | + | 25% (1/4) |
| | 0.6 | + | 0% (0/5) |
| *Bordetella* | 0 | unknown | 50% (2/4) |
| *parapertussis* | 0.2 | + | 0% (0/3) |
| | 0.6 | − | 0% (0/4) |

The vaccine efficacy was determined to be + when a significant difference ($P<0.05$) was detected between the unvaccinated group and the vaccinated group in an experimental respiratory tract infection system (experimental spray infection system or experimental transnasal infection system).

The mouse fatality rate describes the number of mouse deaths due to the vaccination in each experimental group.

Preferred inactivation conditions used in the present invention include weak conditions as described below. First, formaldehyde is added to a live cell suspension of *B. parapertussis* at a final concentration of 0.2%, and the suspension is left to stand at room temperature for 1 to 5 days, preferably 3 days, for inactivation. Thereafter, the suspension is centrifuged at 5,000 rpm for 10 minutes, the supernatant is removed, and the cells are suspended in an equal amount of phosphate buffered saline (0.01 M, pH 7.2) to produce an inactivated *B. parapertussis* suspension. Completion of inactivation can be confirmed by withdrawing a portion of the inactivated sample and confirming that the bacteria do not grow when incubated. After inactivation treatment, chemical reagents used for the inactivation are removed by washing with phosphate buffer or such. Then, the number of bacteria is adjusted to approximately $1\times10^{10}$ cells/mL. In the present invention, a preferred cell concentration is approximately $1\times10^{10}$ cells/mL.

Aliquots (for example, 0.5 mL, 1.0 mL, or 10 mL) of the aforementioned *B. parapertussis* suspension or antigen protein solution are placed in vials or syringes to produce the vaccines.

An example of the composition of a general *B. parapertussis* vaccine is as follows, but the vaccine composition is not limited thereto.

Antigen: inactivated whole *Bordetella parapertussis* bacteria; cell concentration of $1\times10^{10}$ cells/mL Buffer: 0.01 M phosphate buffered saline pH: 7.0

Osmotic pressure: 1

Volume: 0.6 mL

Preservatives: 2% sorbitol and 5% lactose

Pharmaceutically acceptable additives may be added to the vaccine preparation of the present invention. Herein, "pharmaceutically acceptable additives" refer to pharmaceutically acceptable material that are substances different from the antigen (or immunogen) and that can be administered with an antigen during vaccination. Examples include vaccine additives such as adjuvants, preservatives, and stabilizers, but are not limited thereto. Without limitation, adjuvants such as aluminum phosphate, aluminum hydroxide, and MF59 may be used as approved adjuvants for use in human vaccines.

Without limitation, about 0.2% gelatin or dextran, 0.1-1.0% sodium glutamate, approximately 5% lactose, approximately 2% sorbitol, or such may be used as a stabilizer. Without limitation, about 0.01% thimerosal, about 0.1% beta-propionolactone, about 0.5% phenoxyethanol or such may be used as a stabilizer.

Injections are prepared by adding pH-control agents, buffers, stabilizers, preservatives or such if necessary and made into subcutaneous, intramuscular, and intravenous injections by common procedures. An injection can be prepared as a solid formulation before use by, for example, freeze-drying a solution stored in a container. A single dose can be filled in a container, or multiple doses may be filled in one container.

Various known methods can be used for administering bacterial vaccines of the present invention. Vaccines are administered by preferably subcutaneous injection, intramuscular injection, intranasal administration, oral administration, percutaneous administration and such, and more preferably by intramuscular injection, but are not limited thereto. Examples of intranasal administration include intranasal sprays, powder sprays, drops, swabs and the like. Among these methods of vaccination, oral inoculation and intranasal inoculation are more preferable, because the respiratory tract and digestive tract mucous membranes are important sites at early stages of infection. By inoculating a vaccine comprising appropriate adjuvants having strong immunity-enhancing activities, immune mechanism is induced at local mucous membrane and protective effects can be exhibited at the earliest possible stages of infection.

A suitable vaccination method is determined by considering the type of vaccine antigen, dosage form, timing of antibody expression, duration of antibody persistence, age of the subject receiving vaccine, and such. Besides humans, examples of the subject to be inoculated include pet animals, domestic animals, wild animals and birds. The method of vaccination is ultimately determined through clinical testing by specialists, and these methods are well known to those skilled in the art. The product may be for single inoculation or for multiple inoculations. The dosage changes depending on the weight and age of the patient, the method of administration and such, but those skilled in the art can appropriately select a suitable dose.

When the vaccine composition of the present invention is adjusted to a final cell concentration of $10^{10}$ cells/mL, it can be administered to mice at a dose of 0.100 mL/kg body weight to 3 mL/kg body weight.

On the other hand, while whole-cell vaccines generally used for humans can be subcutaneously or intramuscularly injected at a dose of 0.1 to 0.5 mL, the vaccine of the present invention can be administered at ⅓ to 1/30 of the dose of vaccine formulations produced by the same method and containing *B. pertussis* as an antigen.

For example, when humans are inoculated with the vaccine of the present invention, 0.02 to 0.5 mL of the vaccine formulation having the above-mentioned composition (final cell concentration of $10^{10}$ cells/mL) can be administered.

The administration frequency of the vaccine of the present invention may be once or multiple times, but is preferably twice to four times, and is most preferably four times.

Determination of vaccine efficacy is important in vaccine development. While these tests are well known to vaccine professionals, an example of the methods is described below: Antigenic materials which possibly contain a protective antigen or an antigen that prevents disease onset are inactivated, and then laboratory animals are immunized. Next, the immunized animals are challenged with *Bordetella parapertussis*, and the effectiveness of the test materials is determined from the viability of the laboratory animals, decrease in the number of infecting *Bordetella parapertussis* cells, and the like. *Bordetella parapertussis* infects humans to develop the disease, and it is also known to establish experimental infection in mice. Methods that are more suitable for laboratory animals are determining whether they are alive or dead, or measuring the degree of *Bordetella parapertussis* infection in the lung.

*B. parapertussis* cells, preparations thereof, or whole-cell bacterial vaccine compositions of the present invention can induce immunity against *B. parapertussis* infection in inoculated subjects.

Therefore, the present invention's whole cells, whole-cell homogenates, cell lysates of *B. parapertussis*, or whole-cell bacterial vaccine compositions comprising them as antigens can be used to prevent whooping cough caused by *B. parapertussis.*

All prior art references cited herein are incorporated by reference into this description.

EXAMPLES

Figure 1:
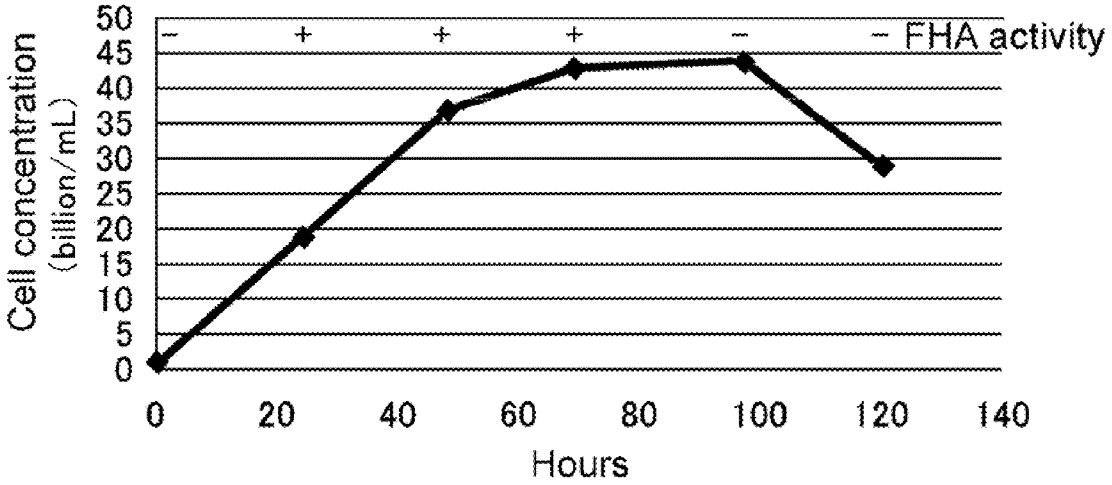
FIG. 1 shows the relationship between the culturing time for *B. parapertussis*, the bacterial cell concentration, and the presence or absence of filamentous hemagglutinin (FHA). *B. parapertussis* was suspended in a Stainer-Scholte liquid medium supplemented with casamino acids at one billion cells/mL, and 10 mL of the suspension was placed in a 75-$cm^2$ culturing flask and subjected to a static culture at 37° C. The culture solution was collected after 24, 48, 72, 96, and 120 hours of culture, and the bacterial concentration and hemagglutination activity (FHA activity, used as an index of virulence factor production) were measured. *B. parapertussis* proliferated until after 72 hours and then showed a decrease in cell concentration, which appeared to be due to bacteriolysis. FHA activity was detectable in a 100-fold diluted culture solution between 24 to 72 hours, but could not be detected thereafter. From these results, the optimum incubation time for a vaccine material was considered to be 72 hours.

Hereinbelow, the present invention will be specifically described with reference to the Examples, but it is not to be construed as being limited thereto.

Composition of the Media Used in the Present Invention

| <Bordet-Gengou medium> | |
|---|---|
| Sodium chloride | 5.5 g |
| Agar | 20 g |
| Potato exudate containing 1% glycerol | 1 L |

After sterilization at 121° C. for 15 minutes, 150 mL of defibrinated sheep blood was added. When a drug-resistant bacterial strain was used, an appropriate antibiotic was added. In the above-mentioned case, 200 μg/mL of streptomycin was used.

| <Charcoal agar medium> | |
|---|---|
| Beef heart extract | 12 g |
| Peptone | 10 g |
| Sodium chloride | 5 g |
| Soluble starch | 10 g |
| Yeast extract solution | 3.5 g |
| Charcoal powder | 4 g |
| Agar | 18 g |
| Ultrapure water | 1 L |

After sterilization at 121° C. for 15 minutes, 100 mL of defibrinated sheep blood was added. When a drug-resistant bacterial strain was used, an appropriate antibiotic was added. In the above-mentioned case, 200 μg/mL of streptomycin was used.

| <Stainer-Scholte liquid medium supplemented with casamino acids> | |
|---|---|
| Sodium glutamate | 10.72 g |
| Proline | 0.24 g |
| Sodium chloride | 2.0 g |
| Potassium dihydrogen phosphate | 0.5 g |
| Potassium chloride | 0.2 g |
| Tris hydrochloride | 3.175 g |
| Tris | 0.587 g |
| Magnesium chloride hexahydrate | 0.1 g |
| 1 M Calcium chloride solution | 0.135 mL |
| Casamino acids | 2.5 g |
| 5% Starch solution | 10 mL |

The above were mixed with ultrapure water to produce 1 L of solution, and then sterilized at 121° C. for 15 minutes. After allowing the solution to cool down, the following solution sterilized by filtration was added.

| | |
|---|---|
| L-cysteine | 0.04 g |
| Ferric sulfate heptahydrate | 0.01 g |
| Ascorbic acid | 0.02 g |
| Reduced glutathione | 0.1 g |

The above were dissolved using a small amount of hydrochloric acid and ultrapure water to produce 10 mL solution.

Test Example 1

Preparation of Pertussis Vaccine

An existing acellular pertussis vaccine (aP) and whole-cell pertussis vaccine (wP) were used as existing control vaccines.

The acellular vaccine used was a commercially-available precipitation-purified mixed diphtheria, tetanus, and pertussis vaccine (DTaP, Kitasato Institute).

The whole-cell pertussis vaccine was prepared as follows. Specifically, cryopreserved *Bordetella pertussis* phase I Tohama strain was spread onto a Bordet-Gengou medium and incubated at 37° C. for four days. From the produced colonies, several showing a hemolytic zone were selected, spread on a charcoal agar medium and incubated at 37° C. for one day. Thereafter, the cells were further spread on a charcoal agar medium, and cultured at 37° C. for four days for enrichment. After completion of culture, the bacterial cells on the surface of the medium were scraped, and then suspended in sterilized physiological phosphate buffered saline. After adjusting the bacterial cell concentration to $10^{10}$ cells/mL, a formaldehyde solution was added to a final formaldehyde concentration of 0.2%. This was gently stirred and then left to stand at 4° C. for three days. After standing, this was centrifuged (5,000 rpm, 4° C., 10 minutes) to remove the supernatant, and the centrifuged precipitate was suspended in sterilized physiological phosphate-buffered saline. This was centrifuged again under the same conditions, and the centrifuged precipitate was suspended in sterilized physiological phosphate-buffered saline. It was then adjusted to be equivalent to a cell concentration of $10^{10}$ cells/mL by adding sterilized physiological phosphate-buffered saline, and this was used as the whole-cell pertussis vaccine.

Test Example 2

Comparison of Virulence Between *Bordetella Pertussis* and *Bordetella parapertussis*

Figure 6:
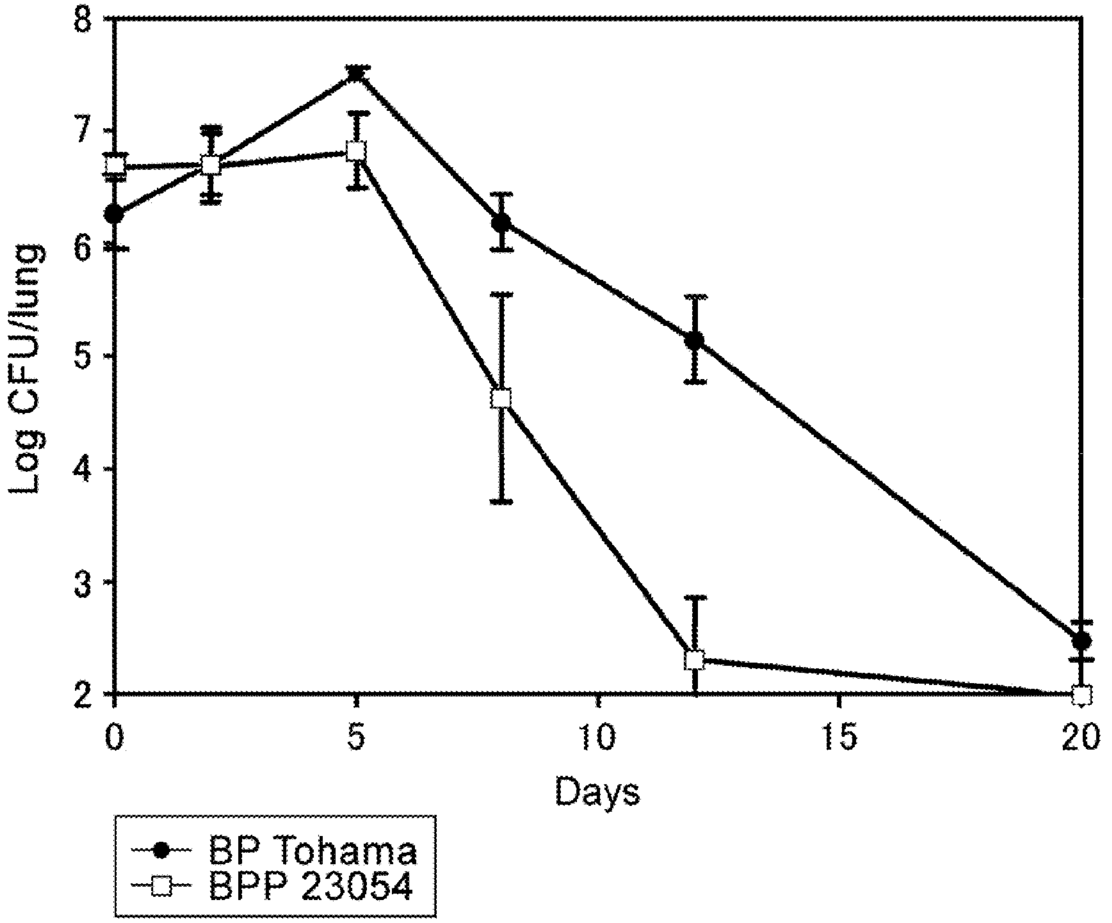
FIG. 6 shows the results of examining changes in the number of viable bacterial cells in the lungs of unvaccinated mice that were transnasally infected with *Bordetella pertussis* (filled circle) or *Bordetella parapertussis* (open square). The results showed that *B. parapertussis* was cleared somewhat faster than *B. pertussis*. Accordingly, *B. parapertussis* was expected to have lower virulence than *B. pertussis*.

Mice (six weeks old) were transnasally infected with a suspension of *B. pertussis* or *B. parapertussis* (viable cell concentration of approximately $10^8$ CFU/mL, 50 μL/mouse) under pentobarbital anesthesia (0.5 mL of 20-fold diluted nembutal solution was injected intraperitoneally). The mice were painlessly killed using pentobarbital after 0 (approximately two hours) and 2 to 20 days, and the lungs were removed aseptically and homogenized in 10 mL of sterile buffered physiological saline. The homogenate was serially diluted, smeared and cultured on a Bordet-Gengou medium (37° C., 4 to 5 days). Then, the number of viable cells of each bacteria in the lung was determined by counting the number of colonies produced. In mice infected with *B. pertussis*, the viable cell count in the lungs increased up to five days after infection, and then decreased gradually (FIG. 6). On the other hand, mice infected with *B. parapertussis* showed almost no increase in the number of cells after infection, and a more rapid decrease than in the *B. pertussis*-infected mice (FIG. 6). These results indicated that the virulence of *B. parapertussis* may be lower than that of *B. pertussis*.

Example 1

*Bordetella parapertussis* Vaccine

Evaluation of Methods for Culturing Cells which are to Become the *B. parapertussis* Vaccine

*B. parapertussis* cells were suspended in Stainer-Scholte liquid medium supplemented with casamino acids at one billion cells/mL. Ten mL of the suspension was placed in a 75-cm$^2$ culture flask and a static culture was conducted at 37° C. This condition is close to that of solid plate culture in terms of the depth of the medium and the standing-still conditions, and allows quantification of cell proliferation, which is difficult in solid plate culture. Furthermore, the Stainer-Scholte liquid medium supplemented with casamino acids contains sufficient nutrients for the proliferation of *B. parapertussis*, as in the charcoal medium. Meanwhile, to produce a vaccine, the bacterial cells must retain their virulence. To confirm this, the presence of filamentous hemagglutinin, which is one of the virulence factors, was measured at each time point using the hemagglutination reaction in 100-fold diluted culture solution as an index.

The obtained results are shown in FIG. 1. *B. parapertussis* proliferated up to day 3 to 4 of culture, and then underwent bacteriolysis. Filamentous hemagglutinin was detectable from day 1 to 3, after which it could not be detected. The fact that cell lysis may result in the release of various types of toxins including endotoxins, and that virulence index disappears on day 4 and after, suggested that cells cultured for 1-3 days can withstand use as vaccine materials, and most suitable are those on day 3.

Based on the above evaluation result, a *B. parapertussis* vaccine containing *B. parapertussis* cells and components produced by *B. parapertussis* were prepared as follows: Cryopreserved *B. parapertussis* cells were spread on a Bordet-Gengou medium, and then incubated at 37° C. for three days. From the produced colonies, several showing a hemolytic zone were selected, spread on a charcoal agar medium, and cultured at 37° C. for one day.

Thereafter, the cells were further passaged on a charcoal agar medium and cultured at 37° C. for three days for enrichment. After completion of culture, the bacterial cells on the surface of the medium were scraped and suspended in sterilized physiological phosphate buffered saline.

The sterilized physiological phosphate buffered saline solution was prepared as follows.

| | |
|---|---|
| Sodium chloride | 8 g |
| Potassium chloride | 0.2 g |
| Disodium hydrogen phosphate | 1.44 g |
| Potassium dihydrogen phosphate | 0.24 g |
| Ultrapure water | 1 L |

This was sterilized at 121° C. for 15 minutes before use.

After the bacterial cell concentration was adjusted to $10^{10}$ cells/mL, a formaldehyde solution was added to a final formalin concentration of 0.2%. This was gently stirred and then left to stand at 4° C. for three days. After standing, this was centrifuged (5,000 rpm, 4° C., 10 minutes) to remove the supernatant, and the centrifuged precipitate was suspended in sterilized physiological phosphate-buffered saline. This was centrifuged again and the centrifuged precipitate was suspended in sterilized physiological phosphate-buffered saline. Then the suspension was adjusted to be equivalent to a cell $10^{10}$ cells/mL, and used as the *B. parapertussis* vaccine.

Example 2

Detection of Infection-Protective Activity (Efficacy) of the Vaccines

The infection protective activity (efficacy) of the respective vaccines was determined using the transnasal infection method for mice, which have a strong correlation with the vaccine effect in humans (Guiso, N. et al., Vaccine 17:2366-2376, 1999). More specifically, each vaccine was inoculated subcutaneously to mice (3.5 weeks old) at a dose of 0.125 mL (corresponding to ¼ single human dose, SHD), and 14 days later, a booster inoculation (the same amount) was carried out. Fourteen days following the booster inoculation, the mice were transnasally infected with the *B. parapertussis* suspension (viable cell concentration of approximately $10^8$ CFU/mL, 50 μL/mouse) under pentobarbital anesthesia (0.5 mL of 20-fold diluted nembutal solution was injected intraperitoneally). The mice were painlessly killed using pentobarbital after 0 (approximately two hours), 2, 5, and 8 days, and the lungs were removed aseptically and homogenized in 10 mL of sterile physiological buffered saline. The homogenate was serially diluted, smeared onto a Bordet-Gengou medium, and cultured (37° C., 4 to 5 days). Then the number of colonies produced was counted to determine the number of viable *B. parapertussis* in the lungs. If infection protection is induced by the vaccine (namely, the effect of the vaccine is observed), the induced infection protective immunity will clear the transnasally infected *B. parapertussis*, and therefore the number of viable bacterial cells in the lungs will be decreased in comparison to the unvaccinated negative control group.

Figure 2:
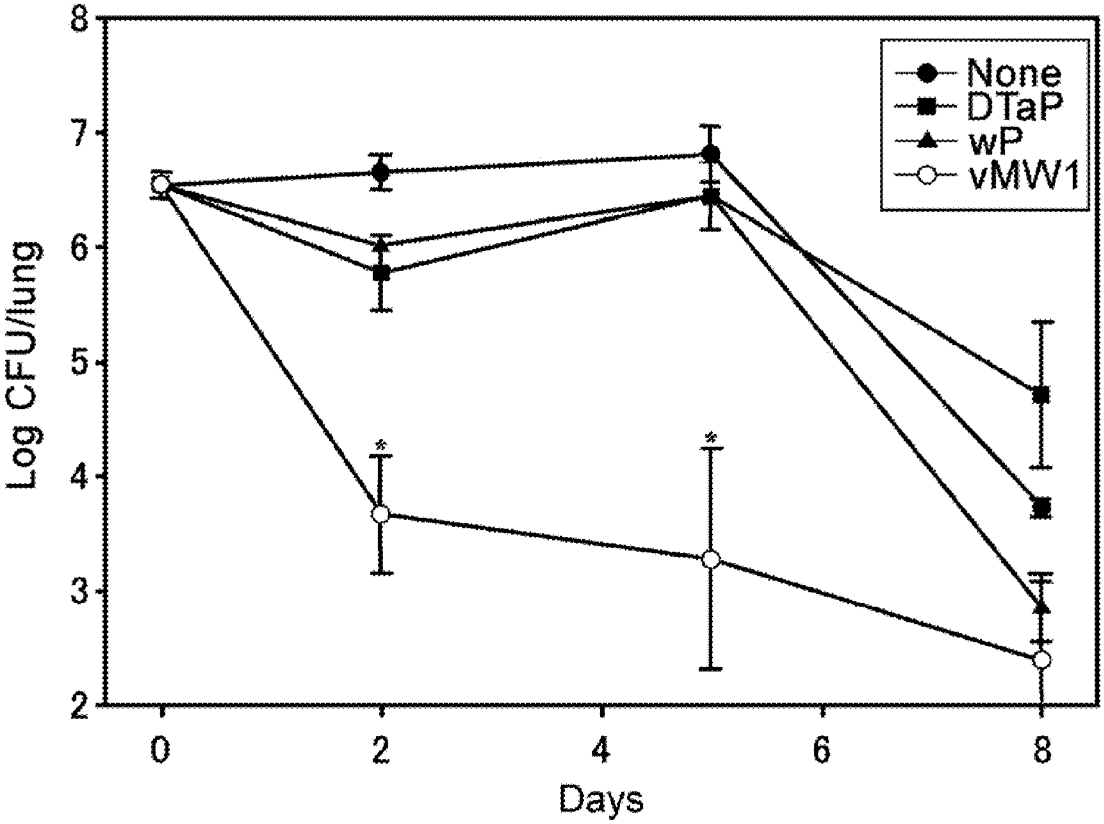
FIG. 2 shows the result of measuring the effect of each vaccine against *Bordetella parapertussis* using an experimental mouse transnasal infection system. Vaccines having an infection protective effect reduce the number of viable *B. parapertussis* bacteria in the lungs in comparison to that in the unvaccinated group (filled circle, None). An existing pertussis vaccine (filled square) and whole-cell pertussis vaccine (filled triangle) showed no significant difference from the unvaccinated group. On the other hand, the *B. parapertussis* vaccine (open circle, vMW1) showed a statistically significant decrease in the number of viable bacterial cells in the lungs, demonstrating its effectiveness as a vaccine. *: significantly different from the negative control group (None) ($p<0.05$).

Protective Effect of the Respective Vaccines against *Bordetella parapertussis* Infection The unvaccinated negative control group (None) showed a gradual increase of viable *B. parapertussis* cells in the lung up to day 5 of infection, followed by a decrease on day 8 (FIG. 2). For the group vaccinated with the existing precipitation-purified mixed diphtheria, tetanus, and pertussis vaccine (DTaP) and the group vaccinated with the whole-cell pertussis vaccine (wP), the viable bacterial cell count in the lungs at each data point did not differ significantly from the value of the negative control group, indicating that these vaccines were not effective against *B. parapertussis* infection (FIG. 2). On the other hand, for the *B. parapertussis* vaccine (vMW1), the viable cell count of *B. parapertussis* in the lungs was significantly lower than the negative control group at each point from day 2 to day 8 of infection, demonstrating that this vaccine is effective against *B. parapertussis* (FIG. 2).

The above results proved that the existing pertussis vaccines have no vaccine effect against *B. parapertussis* infection. This fact has already been found by clinical trials, and confirms that there is a strong correlation of the vaccine effect between the murine experimental system used in the present experiment and humans.

The *B. parapertussis* vaccine invented by the present inventors had a vaccine effect against *B. parapertussis*. The *B. parapertussis* vaccine was produced by scraping *B. parapertussis* grown on a medium, suspending them, and treating them with an inactivator (in this case, formalin). The scraped *B. parapertussis* cells contain secreted factors in addition to cellular components, and some of them may serve as protective antigens.

Example 3

Dose Response of the *Bordetella parapertussis* Vaccine

Figure 3:
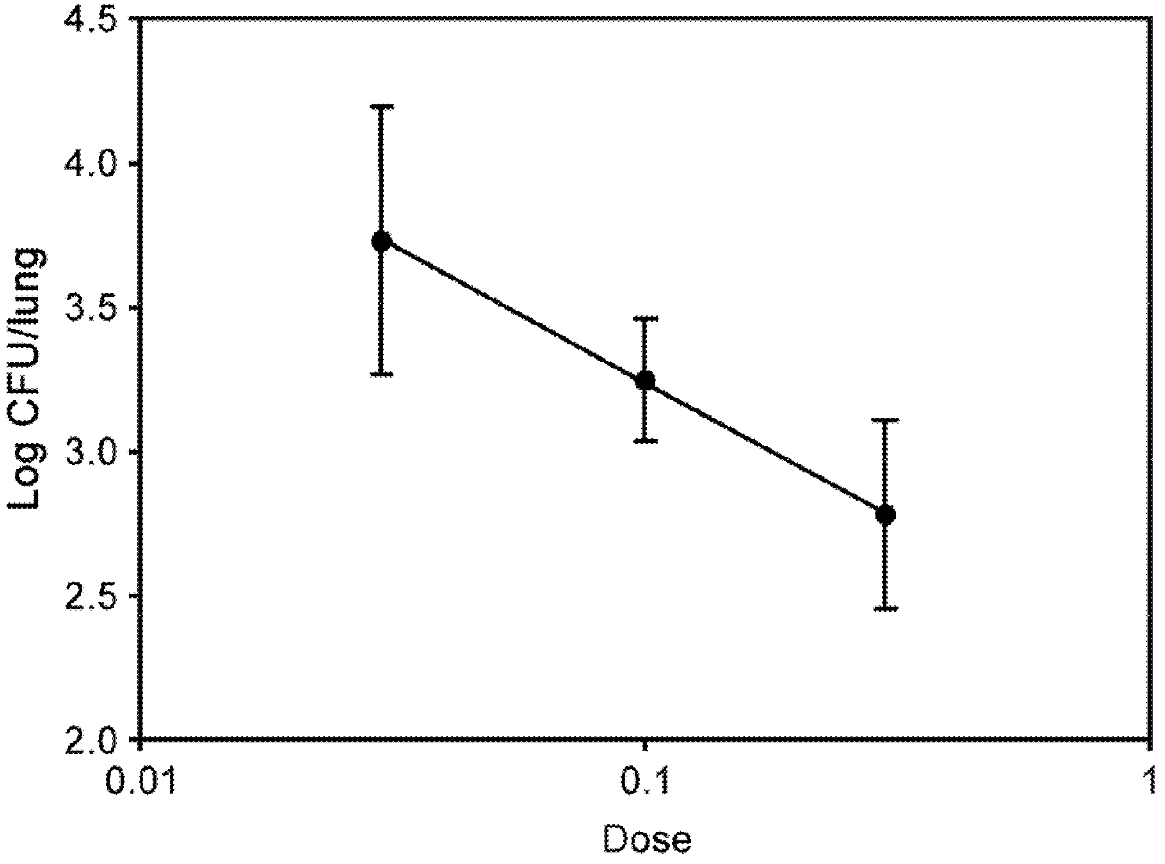
FIG. 3 shows the dose-responsiveness of the *B. parapertussis* vaccine in mice. The normal inoculum dose in the experimental mouse transnasal infection system (0.125 mL) is defined as 1, and the number of viable bacterial cells in the lungs on day 5 after infection in groups inoculated with one-third (0.3 dose), one-tenth (0.1 dose), and one-thirtieth (0.03 dose) of this dose is shown. Only the data for 0.3, 0.1, and 0.03 doses are shown in the figure. The number of viable bacterial cells in the lungs in the unvaccinated group was approximately $10^7$ CFU (7.03±0.02 (Log CFU/lung)), whereas vaccine effects were detected at all inoculum doses shown in the figure. Furthermore, the data from mice and the corresponding inoculum dose in humans (predicted from correlation) are shown below the figure. It was predicted that inoculation of 0.02 to 0.5 mL of this vaccine would be effective in humans.

The *B. parapertussis* vaccine diluted 3-fold, 10-fold, and 30-fold was inoculated into mice and the dose responsiveness was examined. The results are expressed as viable cell count in the lungs after two days of transnasal infection (FIG. 3). As a result, dose responsiveness was confirmed. The *B. parap-*

*ertussis* vaccine exhibited an infection protective effect even at the 1/30 dose. According to this result, the inoculum dose that showed effectiveness in the murine experimental system was approximately 0.1 mL/kg body weight (0.003 mL per mouse).

In the murine experimental system used in the present invention, inoculation of 0.125 mL (1/4 SHD) is the standard for confirming the vaccine effect. If this dose is found to be effective, it correlates to the effectiveness of 0.5-mL inoculation in humans. Therefore, this vaccine may also show effectiveness at a dose of 0.015- to 0.5-mL when used for humans.

From the above results, the *B. parapertussis* vaccine of the present invention was highly anticipated to be effective as a vaccine.

Example 4

Figure 4:
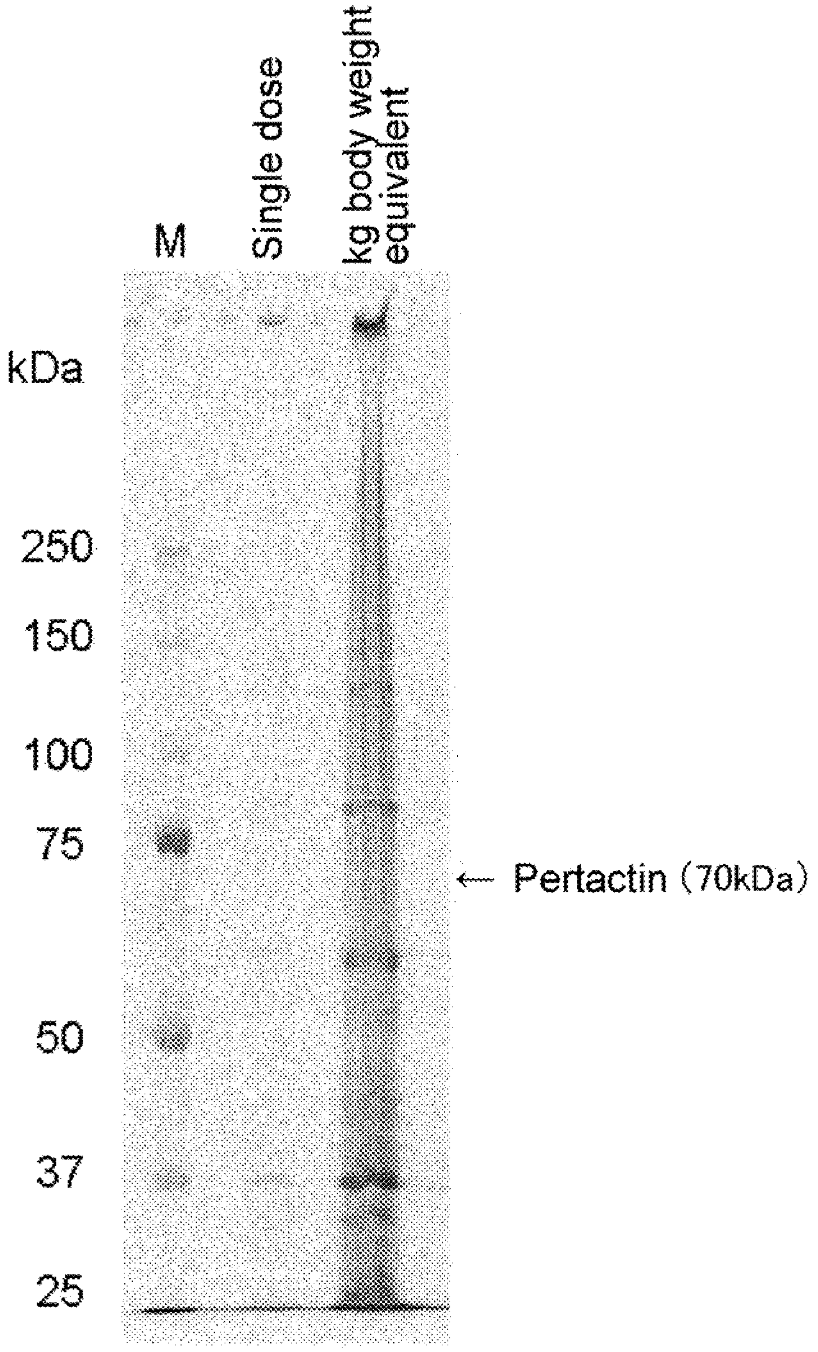
FIG. 4 is a photograph showing the results of analyzing the proteins included in the parapertussis vaccine by SDS-PAGE. ReadyGel J manufactured by Bio-Rad was used for SDS-PAGE, and Biosafe Coomassie solution from the same company was used for staining. The single inoculum dose ($10^{10}$ cells/mL, 0.125 mL) for a mouse and approximately 30 times that amount (per kg body weight of mouse) were loaded and analyzed to obtain the pattern shown in the figure. Pertactin, which shows a molecular weight of approximately 70 kDa, was not detected in either lane.
Figure 5:
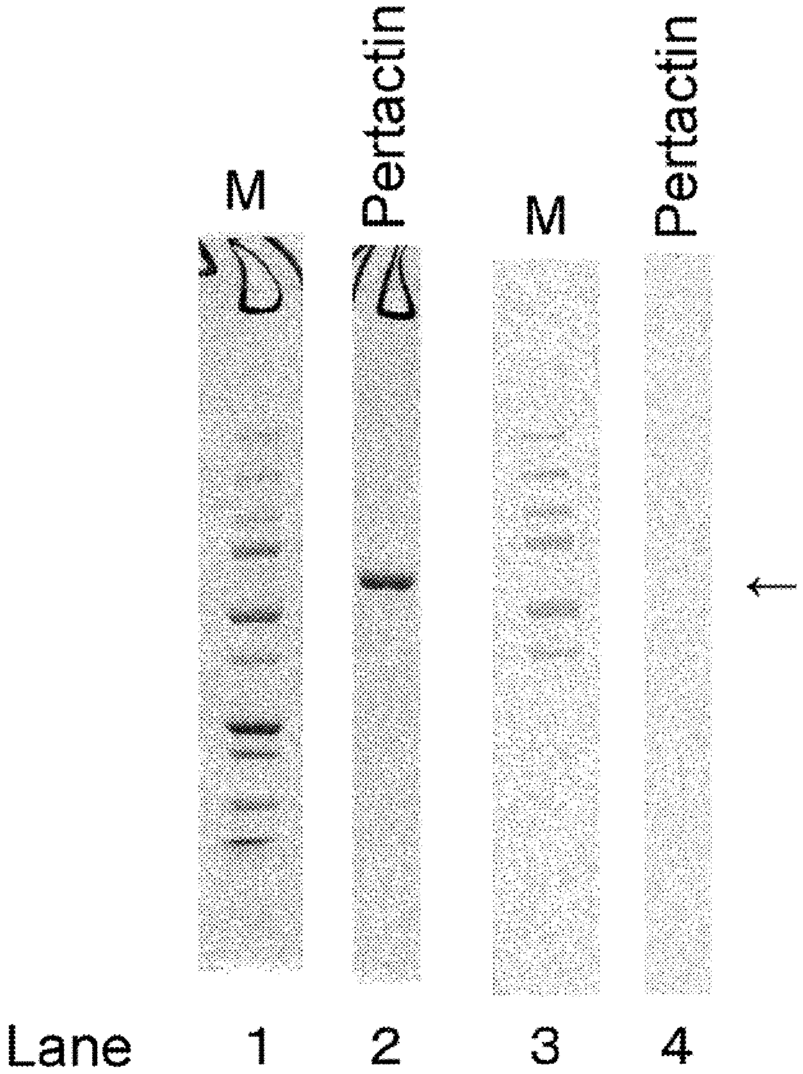
FIG. 5 is a set of photographs showing the results of Western blotting analysis performed to confirm whether immune response reaction against pertactin occurred. Three μg of pertactin purified from *B. pertussis* (sharing common antigenicity with *B. parapertussis*) was subjected to SDS-PAGE, and was transferred onto a nitrocellulose membrane from the developed gel. As a primary antibody, the serum (diluted 1000 times) of a mouse that was inoculated with the *B. parapertussis* vaccine to induce its vaccine effect was used. A 5000-times diluted alkaline phosphatase-labeled anti-mouse IgG (Jackson ImmunoResearch laboratory, U.S.A.) was used as a secondary antibody, and NBT/BCIP was used to detect mouse antibodies bound to pertactin according to a conventional method. If pertactin antibodies are present, a black band is detected at a position of approximately 70 kDa (lane 2, control). However, the result showed that no such antibodies were detected (lane 4). This result revealed that the parapertussis vaccine hardly induced pertactin antibodies.

Examination of the Antigenicity of Pertactin in the Vaccine of the Present Invention When the pertactin content in the *B. parapertussis* vaccine of the present invention was analyzed by SDS-PAGE, it was not detected (FIG. 4). As calculated from the sensitivity of this detection system, the amount of the vaccine used per kg body weight of animal was considered to contain approximately 0.01 μg or less pertactin. This is much lower than the amount of pertactin protein (1 μg/kg) generally required when used as an antigen for inducing an immune response (Japanese Patent Application No. 2003-533990). Furthermore, when mice inoculated with this vaccine were examined for an immune response against pertactin by the Western blotting method, such was not detected in the immunized mice (FIG. 5). Therefore, pertactin and its immune response were considered to be hardly involved in the effect of the *B. parapertussis* vaccine of the present invention.

INDUSTRIAL APPLICABILITY

The present invention provides a whole-cell bacterial vaccine composition for preventing whooping cough caused by *Bordetella parapertussis*, comprising whole cells, whole-cell homogenate, or cell lysate of *B. parapertussis*, as an immunogen.

Pertussis vaccines that are widely used today have little or no effect on whooping cough caused by *B. parapertussis* infection. The vaccine composition of the present invention is useful for preventing whooping cough caused by *B. parapertussis*, which has symptoms not very different to those caused by *B. pertussis*. The *B. parapertussis* vaccines of the present invention exhibit an infection protective effect even at 1/30 of the ordinary dose of the pertussis vaccine. Therefore, they are highly effective vaccines and can be used safely in a small amount.

Furthermore, since the inactivation in the vaccine production process is carried out under conditions weaker than those used for ordinary whole-cell vaccines, the amount of inactivator used during the vaccine production may be small, and the inactivation treatment is simple.

The invention claimed is:

1. A method for preventing whooping cough caused by *B. parapertussis* in a subject, the method comprising steps of:

(a) culturing *B. parapertussis* cells at 35° C. to 37° C. using filamentous hemagglutinin (FHA) as an index to produce a *B. parapertussis* culture preparation with a final cell concentration of $10^{10}$ cells/mL;

(b) inactivating the *B. parapertussis* cells by adding a formalin solution comprising formaldehyde at a final concentration of 0.2% to the *B. parapertussis* culture preparation; and (c) administering the inactivated *B. parapertussis* cells as whole cells, as a whole-cell homogenate thereof, or as a cell lysate thereof to the subject.

2. A method for inducing immunity against *B. parapertussis* in a subject, the method comprising steps of:

(a) culturing *B. parapertussis* cells at 35° C. to 37° C. using filamentous hemagglutinin (FHA) as an index to produce a *B. parapertussis* culture preparation with a final cell concentration of $10^{10}$ cells/mL;

(b) inactivating the *B. parapertussis* cells by adding a formalin solution comprising formaldehyde at a final concentration of 0.2% to the *B. parapertussis* culture preparation; and (c) administering the inactivated *B. parapertussis* cells as whole cells, as a whole-cell homogenate thereof, or as a cell lysate thereof to the subject.

* * * * *

UNITED STATES PATENT AND TRADEMARK OFFICE

CERTIFICATE OF CORRECTION

PATENT NO. : 8,465,754 B2
APPLICATION NO. : 12/601795
DATED : June 18, 2013
INVENTOR(S) : Mineo Watanabe and Eiji Komatsu It is certified that error appears in the above-identified patent and that said Letters Patent is hereby corrected as shown below:

In the Specification

Column 5, line 22: the word “depositary” should be “depository”

Signed and Sealed this
Thirteenth Day of August, 2013

Teresa Stanek Rea
*Acting Director of the United States Patent and Trademark Office*